United States Patent [19]

Ariyoshi et al.

[11] Patent Number: 5,817,886
[45] Date of Patent: Oct. 6, 1998

[54] PROCESS FOR PRODUCTION OF ALKYL ETHER OF PHENOL AND CATALYST USED THEREIN

[75] Inventors: Kimio Ariyoshi; Yuuichi Satoh, both of Suita; Noboru Saito, Takatsuki, all of Japan

[73] Assignee: Nippon Shokubai Co., Ltd., Osaka, Japan

[21] Appl. No.: 772,908

[22] Filed: Dec. 24, 1996

[30] Foreign Application Priority Data

Dec. 28, 1995 [JP] Japan ................................. 7-342277

[51] Int. Cl.⁶ .................................................. C07C 41/09
[52] U.S. Cl. .......................... 568/630; 568/632; 568/658; 568/804; 502/251; 502/341
[58] Field of Search ..................... 568/630, 632, 568/658, 791, 804; 502/251, 341

[56] References Cited

U.S. PATENT DOCUMENTS

| | | |
|---|---|---|
| 4,611,084 | 9/1986 | Mossman . |
| 4,638,098 | 1/1987 | Mossman . |
| 4,675,454 | 6/1987 | Mossman . |
| 4,675,455 | 6/1987 | Mossman . |
| 4,675,456 | 6/1987 | Mossman . |

FOREIGN PATENT DOCUMENTS

| | | |
|---|---|---|
| 0509927 | 10/1992 | European Pat. Off. . |
| 267034A1 | 4/1989 | Germany . |
| 52-36634 | 3/1977 | Japan . |
| 56-25213 | 6/1981 | Japan . |

OTHER PUBLICATIONS

Kagaku Gijutsu Kenkyusho Hokoku Report, vol. 84, No. 5, p. 286, 1989.

*Primary Examiner*—Gary Geist
*Assistant Examiner*—Sreeni Padmanabhan
*Attorney, Agent, or Firm*—Sherman and Shalloway

[57] ABSTRACT

The present invention provides a process for producing an alkyl ether of a phenol from a phenol and an alcohol at a selectivity and a yield higher than in conventional processes, stably over a long period of time. The process is characterized by alkyl-etherifying a phenol with an alcohol in the presence of an oxide catalyst comprising an alkali metal as a constituent element.

15 Claims, No Drawings

PROCESS FOR PRODUCTION OF ALKYL ETHER OF PHENOL AND CATALYST USED THEREIN

The present invention relates to a process for producing an alkyl ether of a phenol. Alkyl ethers of phenols are useful as a raw material for medicines, agricultural chemicals and perfumes, or as an antioxidant, etc.

For alkyl-etherification of phenol, various processes are known such as a process which comprises reacting a phenol with dimethyl sulfate in a strongly alkaline state, and a process which comprises reacting a phenol with a methyl halide in the presence of an aqueous alkali hydroxide solution. These known processes, however, have problems in that toxic substances are handled (this poses a safety and hygienic problem), the raw materials are expensive, and a high cost is required for the disposal of a waste water containing a large amount of inorganic by-products (e.g. sodium sulfate and sodium chloride).

In an attempt to solve the above problems, various studies were made on the alkyl-etherification of phenol using an inexpensive and easy-to-handle alcohol as the etherifying agent.

The above studies include the alkyl-etherifications of phenols by gas-phase reaction. As examples thereof, a process using a boron phosphate catalyst or a catalyst comprising aluminum, boron and phosphorus is disclosed in Japanese Patent Application Kokai (Laid-Open) No. 36634/1977; a process using a kaolin catalyst is disclosed in Japanese Patent Publication No. 25213/1981 and Kagaku Gijutsu Kenkyusho Report, Vol. 84, No. 5, p. 286, 1989; and a process using a zeolite type catalyst is disclosed in former East German Patent DD 267034.

In these processes each using a particular catalyst, the selectivity of alkyl-etherification is increased to a considerably high level, but the amount of ring-methylated product formed as by-product cannot be decreased to zero. The ring-methylated product often has a boiling point close to the boiling point of raw material phenol [for example, 182° C. (boiling point of raw material phenol) vs. 191° C. (boiling point of o-cresol which is a ring-methylated product of raw material phenol); 202° C. (boiling point of raw material p-cresol) vs. 212° C. (boiling point of 2,4-xylenol which is a ring-methylated product of raw material p-cresol)]; and separation of ring-methylated product (by-product) requires a rectifying column having a large number of plates, resulting in high facility cost and high product cost. If the selectivity of alkyl ether could be increased to 100%, distillation and purification becomes unnecessary and a large merit is obtained in industrial production of alkyl ether.

None of the above-mentioned known catalysts has had industrial applicability because they show striking deterioration of activity with the lapse of time owing to, for example, the deposition of carbonaceous substances thereon. Moreover, in the above known processes, there takes place, at a fairly high degree, a dialkyl etherification reaction caused by the intermolecular dehydration between alcohol molecules, making low the recovery ratio of alcohol used as etherifying agent. Therefore, these processes are apparently disadvantageous for use in industry.

As understood from the above, the conventional processes for producing an alkyl ether of a phenol from a phenol and an alcohol, have not been satisfactory from an industrial standpoint. Therefore, it is strongly desired to develop a process capable of producing an alkyl ether of a phenol at a higher selectivity using a catalyst having a stable life.

Hence, the object of the present invention is to provide an improved process for producing an alkyl ether of a phenol from a phenol and an alcohol, i.e. a process which can produce an alkyl ether of a phenol from a phenol and an alcohol at a selectivity and a yield both higher than in conventional processes over a long period of time, with a dialkyl ether (by-product) produced in a small amount and with unreacted raw material alcohol recovered at a high ratio.

The present inventors made an extensive study in order to solve the above-mentioned problems of conventional processes. As a result, the present inventors found out that an alkyl ether of a phenol can be produced at a selectivity far higher than in conventional processes, by etherification of a phenol with an alcohol using an oxide comprising an alkyl metal as a constituent element.

According to the present invention, there is provided a process for producing an alkyl ether of a phenol by reacting a phenol with an alcohol in the presence of a catalyst, wherein the catalyst is an oxide comprising an alkali metal as a constituent element.

In the process of the present invention, the phenol as a raw material is not particularly restricted and includes, for example, phenol derivatives represented by the following general formula (2)

(2)

(wherein R is a hydrogen atom, an alkyl group having 1–4 carbon atoms, an alkoxyl group having 1–4 carbon atoms, a hydroxyl group, a phenyl group, a nitro group, a benzyl group or a halogen atom), and xylenols. Specific examples thereof are monovalent phenols such as phenol, p-cresol, m-cresol, o-cresol, 4-ethylphenol, 4-isopropylphenol, 4-tert-butylphenol, 4-methoxyphenol, 2-ethoxyphenol, 4-phenylphenol, 4-nitrophenol, 4-benzylphenol, 4-chlorophenol and the like; xylenols such as 2,4-xylenol and the like; divalent phenols such as catechol, resorcinol, hydroquinone and the like; and so forth. Of these, monovalent phenols and xylenols are preferred with phenol, p-cresol, m-cresol and o-cresol being particularly preferred.

In the present process, the alcohol as another raw material is not particularly restricted, either, but is preferably a monovalent aliphatic alcohol in view of the reactivity. Examples of the monovalent alcohol are methanol, ethanol, n-propyl alcohol and n-butyl alcohol.

The catalyst used in the present process is not particularly restricted as long as it is an oxide comprising an alkali metal as a constituent element, but is preferably an oxide comprising, as constituent elements, an alkali metal and at least one element selected form the group consisting of elements of groups IIIb, IVb, Vb, VIb, IIIa, IVa and Va of periodic table. The catalyst is more preferably an oxide comprising an alkali metal and silicon and/or zirconium. It is particularly preferably an oxide represented by the following general formula (1):

$$M_a X_b Z_c O_d \qquad (1)$$

(wherein M is an alkali metal; X is silicon and/or zirconium; Z is at least one element selected from Y, La, Ce, Ti, V, Nb, Ta, Cr, Mo, W, B, Al, Ga, In, Tl, Ge, Sn, Pb, P, Sb and Bi; O is oxygen; and a, b, c and d are atom numbers of individual elements with a proviso that when a is 1, b is 1–500, c is 0–1 and d is a number determined by the values of a, b and c and the bonding states of the individual elements).

By the use of the above catalyst, the alkyl etherification of a phenol takes place at a very high selectivity and there is formed substantially no ring-methylated product as by-product. Further, the alcohol used for reaction is consumed selectively for the alkyl etherification of a phenol and there takes place substantially no dialkyl etherification caused by dehydration between alcohol molecules. Furthermore, with the above catalyst, unlike with known catalysts, deposition of carbonaceous substances thereon is very low and, therefore, the catalytic activity is not substantially reduced in continuous long-term use. Even if the catalyst has shown reduction in catalytic activity owing to the coking caused by continuous long-term use under severe conditions, the activity can be recovered by passing of air for burning of the formed coke.

An oxide catalyst comprising only silicon as a constituent metal element and not comprising any alkali metal, i.e. a catalyst consisting of silica alone is a very weak solid acid and accordingly has substantially no activity (see Comparative Example 1 described later; the data shown therein agree with those shown in Table 3 of Reference Example 1 of Japanese Patent Publication No. 25213/1981). It is said that a solid acid having an intermediate acidity is effective for the selective alkyl etherification of a phenol and it is reported that kaolin is most appropriate as such a solid acid (Kagaku Gijutsu Kenkyusho Report, Vol. 84, No. 5, p. 286, 1989). In a reaction using such a solid catalyst having an intermediate acidity, the reduced recovery of alcohol due to ring methylation and dialkyl etherification of alcohol and the reduced catalytic activity due to coking are inevitable. In contrast, the catalyst of the present invention obtained by adding an alkali metal to silica, although its acidity is even lower than that of a catalyst consisting of silica alone, can give an alkyl ether at a very high selectivity as compared with known catalysts. The reason for such a merit of the present catalyst is presumed to be that the very weak solid acidity of the present catalyst can suppress the dialkyl etherification between alcohol molecules and the formation of coke almost completely.

The method for producing the catalyst of the present invention is not particularly restricted and can be any known method.

The method for production of the present catalyst is described below, on a case of producing an oxide comprising an alkali metal and silicon as constituent elements (the oxide is particularly preferable as the present catalyst).

The raw material for alkali metal can be oxides, hydroxides, halides, salts (e.g. nitrates, carbonates, carboxylates, phosphates and sulfates), metals per se, etc. The raw material for silicon can be silicon oxide, silicic acid, silicic acid salts (e.g. alkali metal silicates and alkaline earth metal silicates), organic silicic acid esters, etc. The raw material for Z (which is an optional element) can be oxides, hydroxides, halides, salts (e.g. carbonates, nitrates, carboxylates, phosphates and sulfates), metals per se, etc. The method for catalyst production includes, for example, (1) a method which comprises dissolving or suspending an alkali metal source and a silicon source in water, heating and concentrating the resulting solution or suspension with stirring, drying the resulting concentrate, followed by molding and calcination, (2) a method which comprises immersing a molded silicon oxide in an aqueous solution of an alkali metal source, heating them to dryness, followed by drying and calcination, and (3) a method which comprises mixing a silicic acid salt or a silicon-containing oxide with an aqueous solution of an alkali metal source, followed by drying, molding and calcination. In order to allow the present catalyst to contain Z (an optional element), there is used an alkali metal source and/or a silicon source both containing Z, or a raw material for Z is added in the middle of catalyst production.

The catalyst of the present invention can be used by loading on or mixing with a known carrier (e.g. alumina or silicon carbide).

The calcination temperature used in production of the present catalyst varies depending upon the kinds of catalyst raw materials used, but can be in a wide range of 300°–1,000° C., preferably a range of 400°–800° C.

The process of the present invention can be carried out by any of gas-phase process and liquid-phase process. When the present process is carried out by liquid-phase process, any of batch type operation and flowing type operation can be employed. When the present process is carried out by gas-phase process, any of a fixed bed type reactor and a fluidized bed type reactor can be used.

The raw materials phenol and alcohol are used in a phenol:alcohol molar ratio of 1:1–20, preferably 1:1–10.

When the reaction of the present process is carried out in gas phase, there are employed such a reaction temperature and a reaction pressure that the phenol and alcohol used as raw materials can maintain a gaseous state. The reaction pressure is generally atmospheric pressure or reduced pressure, but may be an applied pressure. The reaction temperature varies depending upon the kinds of phenol and alcohol used and other reaction conditions, but is 250–500° C., preferably 300°–450° C. When the reaction temperature is lower than 250° C., the conversion of raw material phenol is significantly low; when the reaction temperature is higher than 500° C., the selectivity of intended alkyl ether is significantly low. A phenol-alcohol mixed gas is fed to a catalyst layer at atmospheric pressure or under reduced pressure without being diluted or after being diluted with a substance inert to the intended reaction, such as nitrogen, helium, argon, hydrocarbon or the like. The gas hourly space velocity (GHSV) of the phenol-alcohol mixed gas varies depending upon the kinds of raw materials and other reaction conditions, but is in the range of 1–1,000 $h^{-1}$, preferably 10–500 $h^{-1}$.

The present invention is hereinafter described specifically by way of Examples. However, the present invention is in no way restricted to these Examples.

In the Examples, "conversion", "selectivity" and "per-pass yield" have the following definitions.

Conversion (mole %) =
(moles of phenol consumed) ÷
(moles of phenol fed) × 100
Selectivity (mole %) =
(moles of alkyl ether formed) ÷
(moles of phenol consumed) × 100
Per-pass yield (mole %) =
(moles of alkyl ether formed) ÷
(moles of phenol fed) × 100

EXAMPLE 1

[Catalyst production]

30 g of a spherical silica gel (5–10 mesh) was immersed for 2 hours in a solution of 2.71 g of cesium carbonate dissolved in 40 g of water. The resulting material was heated to dryness on a hot water bath, then dried in air at 120° C. for 20 hours, and calcined in air at 500° C. for 2 hours, whereby was produced a catalyst having a composition of $Cs_1Si_{30}$ in terms of atomic ratio when oxygen was excluded.

[Reaction]

20 ml of the catalyst was filled in a stainless steel reaction tube having an inside diameter of 20 mm. The reaction tube was immersed in a molten salt bath of 380° C. Into the reaction tube were fed a phenol-methanol mixture (1:3 molar ratio) and nitrogen so that a raw material gas mixture consisting of 50 volume % of a phenol-methanol mixed gas and 50 volume % of nitrogen was formed in the tube and the space velocity of the phenol-methanol mixed gas became 100 h$^{-1}$, and a reaction was conducted at atmospheric pressure. The reaction product after 1 hour from the start of feeding was analyzed by gas chromatography. As a result, the conversion of phenol was 82.3 mole %, and the selectivity of anisole formation was 100 mole % (per-pass yield of anisole=82.3 mole %). No formation of dimethyl ether was seen and unreacted methanol was recovered nearly quantitatively.

EXAMPLE 2

[Catalyst production]

9.73 g of cesium nitrate was dissolved in 50 g of water. The solution was maintained at 90° C. with stirring, and 30 g of silicon oxide was added thereto. The mixture was concentrated with heating, and the concentrate was dried in air at 120° C. for 20 hours. The resulting solid was crushed to 9–16 mesh and calcined in air at 700° C. for 2 hours, whereby was produced a catalyst having a composition of $Cs_1Si_{10}$ in terms of atomic ratio when oxygen was excluded.

[Reaction]

Using the catalyst, a reaction was conducted in the same manner as in Example 1. After 1 hour from the start of feeding, the conversion of phenol was 77.2 mole %; the selectivity of anisole formation was 100 mole %; and the per-pass yield of anisole was 77.2 mole

EXAMPLES 3–6

[Catalyst production]

Catalysts shown in Table 1 (the compositions were each given in atomic ratio when oxygen was excluded) were produced in the same manner as in Example 2 except that 9.73 g of cesium nitrate used in Example 2 was changed to 3.45 g of lithium nitrate (Example 3), 4.25 g of sodium nitrate (Example 4), 5.06 g of potassium nitrate (Example 5) and 7.38 g of rubidium nitrate (Example 6).

[Reaction]

Using each of the catalysts, a reaction was conducted in the same manner as in Example 1. After 1 hour from the start of feeding, the conversions of phenol, the selectivities of anisole formation and the per-pass yields of anisole were as shown in Table 1.

TABLE 1

| Example No. | Catalyst | Conversion (mole %) | Selectivity (mole %) | Per-pass yield (mole %) |
|---|---|---|---|---|
| 3 | $Li_1Si_{10}$ | 27.6 | 100 | 27.6 |
| 4 | $Na_1Si_{10}$ | 39.2 | 100 | 39.2 |
| 5 | $K_1Si_{10}$ | 52.6 | 100 | 52.6 |
| 6 | $Rb_1Si_{10}$ | 76.5 | 100 | 76.5 |

EXAMPLE 7

A reaction was conducted in the same manner as in Example 1 except that p-cresol was used in place of phenol. After 1 hour from the start of feeding, the reaction product was analyzed by gas chromatography. As a result, the conversion of p-cresol was 82.2 mole %; the selectivity of p-methoxytoluene formation was 99.5 mole % (per-pass yield of p-methoxytoluene=81.8 mole %); the selectivity of 2,4-xylenol formation was 0.2 mole %; and the selectivity of 2.4-dimethylanisole formation was 0.3 mole %.

EXAMPLE 8

A reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 64.7 mole %; the selectivity of p-methoxytoluene formation was 99.9 mole % (per-pass yield of p-methoxytoluene=64.6 mole %); and the selectivity of 2,4-xylenol formation was 0.1 mole %.

EXAMPLE 9

A reaction was conducted in the same manner as in Example 1 except that p-cresol was used in place of phenol and a p-cresol-methanol molar ratio of 1:2 was used. After 1 hour from the start of feeding, the reaction product was analyzed by gas chromatography. As a result, the conversion of p-cresol was 69.6 mole %; the selectivity of p-methoxytoluene formation was 99.9 mole % (per-pass yield of p-methoxytoluene=69.5 mole %); and the selectivity of 2,4-xylenol formation was 0.1 mole %.

EXAMPLE 10

[Catalyst production]

A solution of 135.5 g of cesium carbonate dissolved in 2,300 g of water was added to 1,000 g of silicon oxide. The mixture was extruded to obtain pellets each having a diameter of 6 mm and a length of 6 mm. The pellets were dried in air at 120° C. for 20 hours. The resulting pellets catalyst was calcined in air at 500° C. for 2 hours, whereby was produced a catalyst having a composition of $Cs_1Si_{20}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 71.4 mole %; the selectivity of p-methoxytoluene formation was 99.8 mole % (per-pass yield of p-methoxytoluene=71.3 mole %); and the selectivity of 2,4-xylenol formation was 0.2 mole %.

EXAMPLE 11

A reaction was conducted in the same manner as in Example 1 except that p-cresol was used in place of phenol, ethanol was used in place of methanol, and the reaction temperature was changed to 400° C. After 1 hour from the start of feeding, the reaction product was analyzed by gas chromatography. As a result, the conversion of p-cresol was 42.3 mole %, and the selectivity of 1-ethoxy-4-methylbenzene formation was 100 mole % (per-pass yield of 1-ethoxy-4-methylbenzene=42.3 mole %).

EXAMPLE 12

A reaction was conducted in the same manner as in Example 1 except that p-cresol was used in place of phenol, n-butanol was used in place of methanol, and the reaction temperature was changed to 400° C. After 1 hour from the start of feeding, the reaction product was analyzed by gas chromatography. As a result, the conversion of p-cresol was 25.7 mole %, and the selectivity of 1-butoxy-4-methylbenzene formation was 100 mole % (per-pass yield of 1-butoxy-4-methylbenzene 25.7 mole %).

EXAMPLE 13

A reaction was conducted in the same manner as in Example 1 except that o-cresol was used in place of phenol. After 1 hour from the start of feeding, the reaction product was analyzed by gas chromatography. As a result, the conversion of o-cresol was 68.8 mole %, and the selectivity of 1-methoxy-2-methylbenzene formation was 100 mole % (per-pass yield of 1-methoxy-2-methylbenzene=68.8 mole %).

EXAMPLE 14

A reaction was conducted in the same manner as in Example 1 except that m-cresol was used in place of phenol. After 1 hour from the start of feeding, the reaction product was analyzed by gas chromatography. As a result, the conversion of m-cresol was 81.9 mole %, and the selectivity of 1-methoxy-3-methylbenzene formation was 100 mole % (per-pass yield of 1-methoxy-3-methylbenzene=81.9 mole %).

EXAMPLE 15

A reaction was conducted in the same manner as in Example 1 except that 4-methoxyphenol was used in place of phenol. After 1 hour from the start of feeding, the reaction product was analyzed by gas chromatography. As a result, the conversion of 4-methoxyphenol was 53.5 mole %, and the selectivity of 1,4-dimethoxybenzene formation was 100 mole % (per-pass yield of 1,4-dimethoxybenzene=53.5 mole %).

EXAMPLE 16

A reaction was conducted in the same manner as in Example 1 except that 4-benzylphenol was used in place of phenol and the reaction temperature was changed to 350° C. After 1 hour from the start of feeding, the reaction product was analyzed by gas chromatography. As a result, the conversion of 4-benzylphenol was 80.0 mole %, and the selectivity of 4-benzyl-1-methoxybenzene formation was 100 mole % (per-pass yield of 4-benzyl-1-methoxybenzene= 80.0 mole %).

EXAMPLE 17

A reaction was conducted in the same manner as in Example 1 except that 2.4-xylenol was used in place of phenol and the reaction temperature was changed to 350° C. After 1 hour from the start of feeding, the reaction product was analyzed by gas chromatography. As a result, the conversion of 2,4-xylenol was 42.1 mole % and the selectivity of 2,4-dimethylanisole formation was 100 mole % (per-pass yield of 2,4-dimethylanisole=42.1 mole %).

EXAMPLE 18

[Catalyst production]

30 g of a spherical silica gel (5–10 mesh) was immersed for 2 hours in a solution of 0.37 g of cesium hydroxide dissolved in 40 g of water. The resulting material was heated to dryness on a hot water bath, followed by drying in air at 120° C. for 20 hours and calcination in air at 500° C. for 2 hours, whereby was produced a catalyst having a composition of $Cs_1Si_{200}$ in terms of atomic ratio when oxygen was excluded.

[Reaction]

Using the catalyst, a reaction was conducted in the same manner as in Example 1 except that p-cresol was used in place of phenol and the reaction temperature was changed to 400° C. After 1 hour from the start of feeding, the reaction product was analyzed by gas chromatography. As a result, the conversion of p-cresol was 31.9 mole %, and the selectivity of p-methoxytoluene formation was 100 mole % (per-pass yield of p-methoxytoluene=31.9 mole %).

EXAMPLE 19

[Catalyst production]

A catalyst having a composition of $Na_{0.5}K_{0.5}Si_{30}$ in terms of atomic ratio when oxygen was excluded, was produced in the same manner as in Example 1 except that 2.71 g of cesium carbonate was changed to 0.33 g of sodium hydroxide and 0.47 g of potassium hydroxide.

[Reaction]

Using the catalyst, a reaction was conducted in the same manner as in Example 1 except that p-cresol was used in place of phenol and the reaction temperature was changed to 400° C. After 1 hour from the start of feeding, the reaction product was analyzed by gas chromatography. As a result, the conversion of p-cresol was 34.8 mole %, and the selectivity of p-methoxytoluene formation was 100 mole % (per-pass yield of p-methoxytoluene=34.8 mole %).

EXAMPLE 20

[Catalyst production]

1.32 g of cesium carbonate was dissolved in 50 g of water. The solution was stirred at 90° C. Thereto was added 30 g of zirconium oxide. The mixture was heated and concentrated. The concentrate was dried in air at 120° C. for 20 hours. The resulting solid was crushed to 9–16 mesh and calcined in air at 500° C. for 2 hours, whereby was produced a catalyst having a composition of $Cs_1Zr_{30}$ in terms of atomic ratio when oxygen was excluded.

[Reaction]

Using the catalyst, a reaction was conducted in the same manner as in Example 1 except that p-cresol was used in place of phenol. After 1 hour from the start of feeding, the reaction product was analyzed by gas chromatography. As a result, the conversion of p-cresol was 22.8 mole %, and the selectivity of p-methoxytoluene formation was 100 mole % (per-pass yield of p-methoxytoluene=22.8 mole %).

EXAMPLE 21

[Catalyst production]

30 g of silicon oxide was added to a solution of 9.73 g of cesium nitrate and 2.67 g of zirconyl nitrate (dehydrate) dissolved in 100 g of water. The mixture was heated on a hot water bath with stirring, to concentrate to dryness. The resulting material was dried in air at 120° C. for 20 hours, then crushed to 9–16 mesh, and calcined in air at 700° C. for 2 hours, whereby was produced a catalyst having a composition of $Cs_1Si_{10}Zr_{0.2}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 67.3 mole %; the selectivity of p-methoxytoluene formation was 99.9 mole % (per-pass yield of p-methoxytoluene=67.2 mole %); and the selectivity of 2,4-xylenol formation was 0.1 mole %.

EXAMPLE 22

[Catalyst production]

20 g of a spherical silica gel (5–10 mesh) was immersed for 2 hours in a solution of 1.81 g of cesium carbonate and 0.13 g of 85% orthophosphoric acid dissolved in 40 g of water. The resulting material was heated to dryness on a hot water bath, then dried in air at 120° C. for 20 hours, and calcined in air at 500° C. for 2 hours, whereby was produced a catalyst having a composition of $Cs_1Si_{30}P_{0.1}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 66.5 mole %; the selectivity of p-methoxytoluene formation was 99.9 mole % (per-pass yield of p-methoxytoluene=66.4 mole %); and the selectivity of 2,4-xylenol formation was 0.1 mole %.

EXAMPLE 23

[Catalyst production]

40 g of a spherical silica gel (5–10 mesh) was immersed, for 2 hours, in a solution of 8.32 g of aluminum nitrate nonahydrate dissolved in 60 g of water. The mixture was heated to dryness on a hot water bath. The resulting material was dried in air at 120° C. for 20 hours, followed by calcination in air at 500° C. for 2 hours. 20 g of the calcined product was immersed, for 2 hours, in a solution of 4.39 g of cesium carbonate dissolved in 30 g of water. The mixture was heated to dryness on a hot water bath. The resulting material was dried in air at 120° C. for 20 hours, followed by calcination in air at 500° C. for 2 hours, whereby was produced a catalyst having a composition of $Cs_1Si_{12}Al_{0.4}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 73.4 mole %; the selectivity of p-methoxytoluene formation was 99.8 mole % (per-pass yield of p-methoxytoluene=73.3 mole %); and the selectivity of 2,4-xylenol formation was 0.2 mole %.

EXAMPLE 24

[Catalyst Production]

30.0 g of silicon oxide was added to a solution of 19.5 g of cesium nitrate and 1.23 g of boric acid dissolved in 100 g of water. The mixture was heated on a hot water bath with stirring, to concentrate to dryness. The resulting material was dried in air at 120° C. for 20 hours, then crushed to 9–16 mesh, and calcined in air at 700° C. for 2 hours, whereby was produced a catalyst having a composition of $Cs_1Si_5B_{0.2}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 67.8 mole %; the selectivity of p-methoxytoluene formation was 99.8 mole % (per-pass yield of p-methoxytoluene=67.7 mole %); and the selectivity of 2,4-xylenol formation was 0.2 mole %.

EXAMPLE 25

[Catalyst Production]

24.7 g of zirconium oxide was added to a solution of 7.8 g of cesium nitrate and 4.2 g of diammonium hydrogenphosphate dissolved in 40 g of water. The mixture was heated on a hot water bath with stirring, to concentrate to dryness. The resulting material was dried in air at 120° C. for 20 hours, then crushed to 9–16 mesh, and calcined in air at 500° C. for 2 hours, whereby was produced a catalyst having a composition of $Cs_1Zr_5P_{0.8}$ in terms of atomic ratio when oxygen was excluded.

[Reaction]

Using the catalyst, a reaction was conducted in the same manner as in Example 1 except that p-cresol was used in place of phenol. After 1 hour from the start of feeding, the reaction product was analyzed by gas chromatography. As a result, the conversion of p-cresol was 31.8 mole %, and the selectivity of p-methoxytoluene formation was 100 mole % (per-pass yield of p-methoxytoluene=31.8 mole %).

EXAMPLE 26

[Catalyst Production]

30 g of silicon oxide was added to a solution of 17.9 g of disodium hydrogenphosphate (dodecahydrate) dissolved in 100 g of water. The mixture was heated on a hot water bath with stirring, to concentrate to dryness. The resulting material was dried in air at 120° C. for 20 hours, then crushed to 9–16 mesh, and calcined in air at 400° C. for 2 hours, whereby was produced a catalyst having a composition of $Na_1Si_5P_{0.5}$ in terms of atomic ratio when oxygen was excluded.

[Reaction]

Using the catalyst, a reaction was conducted in the same manner as in Example 1 except that p-cresol was used in place of phenol. After 1 hour from the start of feeding, the reaction product was analyzed by gas chromatography. As a result, the conversion of p-cresol was 27.4 mole %, and the selectivity of p-methoxytoluene formation was 100 mole % (per-pass yield of p-methoxytoluene=27.4 mole %).

EXAMPLE 27

[Catalyst Production]

25 g of silicon oxide was added to a solution of 2.26 g of cesium carbonate and 0.53 g of yttrium nitrate hexahydrate dissolved in 40 g of water. The mixture was heated on a hot water bath with stirring, to concentrate to dryness. The resulting material was dried in air at 120° C. for 20 hours, then crushed to 9–16 mesh, and calcined in air at 500° C. for 2 hours, whereby was produced a catalyst having a composition of $Cs_1Si_{30}Y_{0.1}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 28.4 mole %; the selectivity of p-methoxytoluene formation was 99.6 mole % (per-pass yield of p-methoxytoluene=28.3 mole %); and the selectivity of 2,4-xylenol formation was 0.4 mole %.

EXAMPLE 28

[Catalyst production]

25 g of a spherical silica gel (5–10 mesh) was immersed for 2 hours in a solution of 2.34 g of cesium chloride and 1.80 g of lanthanum nitrate hexahydrate dissolved in 50 g of water. The resulting material was heated to dryness on a hot water bath, followed by drying in air at 120° C. for 20 hours and calcination in air at 500° C. for 2 hours, whereby was produced a catalyst having a composition of $Cs_1Si_{30}La_{0.3}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 35.3 mole %; the selectivity of p-methoxytoluene formation was 99.7 mole % (per-pass yield of p-methoxytoluene=35.2 mole %); and the selectivity of 2,4-xylenol formation was 0.3 mole %.

EXAMPLE 29

[Catalyst production]

30 g of a spherical silica gel (5–10 mesh) was immersed for 2 hours in a solution of 2.71 g of cesium carbonate and 1.55 g of an aqueous ammonium metatungstate solution ($WO_3$=50 wt. %) dissolved in 60 g of water. The resulting material was heated to dryness on a hot water bath, followed by drying in air at 1200° C. for 20 hours and calcination in air at 500° C. for 2 hours, whereby was produced a catalyst having a composition of $Cs_1 Si_{30} W_{0.2}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 57.6 mole %; the selectivity of p-methoxytoluene formation was 99.6 mole % (per-pass yield of p-methoxytoluene=57.4 mole %); and the selectivity of 2,4-xylenol formation was 0.4 mole %.

EXAMPLE 30

[Catalyst production]

20 g of silica alumina (pellets of 5 mm in diameter and 5 mm in length; Si/Al ratio=5.5, $SiO_2$=81.6 wt. %, $Al_2O_3$= 12.6 wt. %) was immersed for 2 hours in a solution of 12.2 g of cesium carbonate dissolved in 25 g of water. The resulting material was heated to dryness on a hot water bath, followed by drying in air at 120° C. for 20 hours and calcination in air at 500° C. for 2 hours, whereby was produced a catalyst having a composition of $Cs_1Si_{3.67}Al_{0.67}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 76.6 mole %; the selectivity of p-methoxytoluene formation was 99.7 mole % (per-pass yield of p-methoxytoluene=76.4 mole %); and the selectivity of 2,4-xylenol formation was 0.1 mole % and the selectivity of 2,4-dimethylanisole formation was 0.2 mole %.

EXAMPLE 31

[Catalyst production]

A solution of 5.42 g of cesium carbonate dissolved in 40 g of water was stirred at 90° C. Thereto was added 40 g of a commercial kaolin (a product of Wako Pure Chemical Industries, Ltd.). The mixture was heated for concentration. The concentrate was dried in air at 120° C. for 20 hours. The resulting solid was crushed to 9–16 mesh and calcined in air at 500° C. for 2 hours, whereby was produced a catalyst comprising kaolin and 11.7% by weight, based on the weight of kaolin, of cesium oxide supported on kaolin.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 9.9 mole %; the selectivity of p-methoxytoluene formation was 87.3 mole % (per-pass yield of p-methoxytoluene=8.64 mole %); and the selectivity of 2,4-xylenol formation was 6.9 mole % and the selectivity of phenol formation was 5.8 mole %.

EXAMPLE 32

[Catalyst production]

A solution of 9.80 g of cesium carbonate dissolved in 40 g of water was stirred at 90° C. Thereto was added 80 g of niobium pentsoxide. The mixture was heated for concentration. The concentrate was dried in air at 120° C. for 20 hours. The resulting solid was crushed to 9–16 mesh and calcined in air at 500° C. for 2 hours, whereby was produced a catalyst having a composition of $Cs_1Nb_{10}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 7.3 mole %; the selectivity of p-methoxytoluene formation was 95.5 mole % (per-pass yield of p-methoxytoluene=6.97 mole %); and the selectivity of 2,4-xylenol formation was 2.2 mole % and the selectivity of phenol formation was 2.3 mole %.

EXAMPLE 33

[Catalyst production]

A solution of 5.34 g of cesium carbonate dissolved in 40 g of water was stirred at 90° C. Thereto was added 80 g of a commercial aluminum phosphate [Taipoly L2 (trade name), a product of Taihei Chemical Industry Co., Ltd.]. The mixture was heated for concentration. The concentrate was dried in air at 120° C. for 20 hours. The resulting solid was crushed to 9–16 mesh and calcined in air at 500° C. for 2 hours, whereby was produced a catalyst having a composition of $Cs_1Al_{20}P_{20}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 1.4 mole %; the selectivity of p-methoxytoluene formation was 94.9 mole % (per-pass yield of p-methoxytoluene=1.33 mole %); and the selectivity of 2,4-xylenol formation was 5.1 mole %.

EXAMPLE 34

[Catalyst production]

20 g of boric acid and 37.3 g of 85% orthophosphoric acid were thoroughly stirred at room temperature to form a slurry. Thereto was added a solution of 2.64 g of cesium carbonate dissolved in 5 g of water. The mixture was stirred at 90° C. for concentration. The concentrate was dried in air at 120° C. for 20 hours. The resulting solid was crushed to 9–16 mesh and calcined in air at 500° C. for 2 hours, whereby was produced a catalyst having a composition of $Cs_1B_{20}P_{20}$ in terms of atomic ratio when oxygen was excluded.

[Reaction]

Using the catalyst, a reaction was conducted in the same manner as in Example 1 except that p-cresol was used in place of phenol and the reaction temperature was changed to 350° C. After 1 hour from the start of feeding, the reaction product was analyzed by gas chromatography. As a result, the conversion of p-cresol was 15.5 mole %; the selectivity of p-methoxytoluene formation was 96.7 mole % (per-pass yield of p-methoxytoluene=15.0 mole %); and the selectivity of 2,4-xylenol formation was 3.3 mole %.

EXAMPLE 35

[Catalyst Production]

30 g of silicon oxide was added to a solution of 19.5 g of cesium nitrate and 10.5 g of diammonium hydrogenphosphate dissolved in 80 g of water. The mixture was heated on a hot water bath with stirring, to concentrate to dryness. The resulting material was dried in air at 120° C. for 20 hours, then crushed to 9–16 mesh, and calcined in air at 500° C. for 2 hours, whereby was produced a catalyst having a composition of $Cs_1Si_5P_{0.8}$ in terms of atomic ratio when oxygen was excluded.

[Reaction]

Using the catalyst, a reaction was conducted in the same manner as in Example 1 except that catechol was used in place of phenol and a catechol:methanol molar ratio of 1:6 was used. After 1 hour from the start of feeding, the reaction product was analyzed by gas chromatography. As a result, the conversion of catechol was 64.7 mole %, and the selectivity of 2-methoxyphenol formation was 100 mole % (per-pass yield of 2-methoxyphenol=64.7 mole %).

EXAMPLE 36

Using the catalyst of Example 1, a reaction was conducted in the same manner as in Example 1 except that resorcinol was used in place of phenol and a resorcinol:methanol molar ratio of 1:6 was used. After 1 hour from the start of feeding, the reaction product was analyzed by gas chromatography. As a result, the conversion of resorcinol was 100 mole %; the selectivity of 3-methoxyphenol formation was 45.7 mole % (per-pass yield of 3-methoxyphenol=45.7 mole %); and the selectivity of 1,3-dimethoxybenzene formation was 54.3 mole % (per-pass yield of 1,3-dimethoxybenzene=54.3 mole %).

EXAMPLE 37

A reaction was conducted in the same manner as in Example 1 except that hydroquinone was used in place of phenol, a hydroquinone:methanol molar ratio of 1:8 was used, and the reaction temperature was changed to 350° C. After 1 hour from the start of feeding, the reaction product was analyzed by gas chromatography. As a result, the conversion of hydroquinone was 100 mole %; the selectivity of 4-methoxyphenol formation was 71.9 mole % (per-pass yield of 4-methoxyphenol=71.9 mole %); and the selectivity of 1,4-dimethoxybenzene formation was 28.1 mole % (per-pass yield of 1,4-dimethoxybenzene=28.1 mole %).

EXAMPLE 38

Into a 100-ml rotary autoclave were fed 2 g of the catalyst of Example 1, 10 g of p-cresol and 14.8 g of methanol (p-cresol:methanol molar ratio=5). The autoclave inside was purged with an inert gas (nitrogen). The autoclave contents were stirred at 300° C. for 5 hours at 280 rpm. After cooling, the reaction product was taken out of the autoclave and analyzed by gas chromatography. As a result, the conversion of p-cresol was 11.7 mole %, and the selectivity of p-methoxytoluene formation was 100% (per-pass yield of p-methoxytoluene=11.7 mole %).

EXAMPLE 39

A stainless steel-made reaction tube was filled with 20 ml of the catalyst of Example 1 and then immersed in a molten salt bath of 380° C. The reaction tube inside was made vacuum by the use of a vacuum pump, and a phenol-methanol mixed liquid (molar ratio=1:3) was fed into the reaction tube by the use of a metering pump so that the space velocity of the mixed gas formed in the tube became 100 h$^{-1}$ and the outlet pressure of the mixed gas became 380 mmHg. The gas after reaction was cooled and collected by a condenser, and the resulting condensate was analyzed by gas chromatography. A reaction was conducted continuously for 100 hours. After that, the feeding of raw materials was stopped and nitrogen was introduced for pressure release. Then, air was passed for 24 hours to burn the carbonaceous substances deposited on the catalyst, whereby the catalyst was regenerated. Thereafter, a reaction was conducted again continuously for 100 hours under the same conditions as mentioned above. The conversion of phenol, the selectivity of anisole formation and the per-pass yield of anisole after 1 hour, 20 hours and 100 hours from the start of raw materials feeding and after 1 hour, 20 hours and 100 hours from the completion of catalyst regeneration were as shown in Table 2.

TABLE 2

| Time (hours) | Conversion (mole %) | Selectivity (mole %) | Per-pass yield (mole %) |
| --- | --- | --- | --- |
| From the start of raw materials feeding | | | |
| 1 | 82.3 | 100 | 82.3 |
| 20 | 78.3 | 100 | 78.3 |
| 100 | 77.7 | 100 | 77.7 |
| From the completion of catalyst regeneration | | | |
| 1 | 79.1 | 100 | 79.1 |
| 20 | 77.3 | 100 | 77.3 |
| 100 | 77.5 | 100 | 77.5 |

EXAMPLE 40

A stainless steel-made reaction tube was filled with 20 ml of the catalyst of Example 1 and then immersed in a molten salt bath of 350° C. A p-cresolmethanol mixed liquid (molar ratio=1:3) was fed into the reaction tube by the use of a metering pump so that the space velocity of the mixed gas formed in the tube became 100 h$^{-1}$, and a reaction was conducted at atmospheric pressure. The gas after reaction was cooled and collected by a condenser, and the resulting condensate was analyzed by gas chromatography. The reaction was conducted continuously for 100 hours. After that, the feeding of raw materials was stopped. Then, air was passed for 24 hours to burn the carbonaceous substances deposited on the catalyst, whereby the catalyst was regenerated. Thereafter, a reaction was conducted again continuously for 100 hours under the same conditions as mentioned above. The conversion of p-cresol, the selectivity of p-methoxytoluene formation and the per-pass yield of p-methoxytoluene after 1 hour, 20 hours and 100 hours from the start of raw materials feeding and after 1 hour, 20 hours and 100 hours from the completion of catalyst regeneration were as shown in Table 3.

TABLE 3

| Time (hours) | Conversion (mole %) | Selectivity (mole %) | Per-pass yield (mole %) |
|---|---|---|---|
| From the start of raw materials feeding | | | |
| 1 | 64.7 | 99.9 | 64.6 |
| 20 | 61.3 | 99.9 | 61.2 |
| 100 | 58.7 | 100 | 58.7 |
| From the completion of catalyst regeneration | | | |
| 1 | 61.1 | 99.9 | 61.0 |
| 20 | 60.2 | 100 | 60.2 |
| 100 | 58.8 | 100 | 58.8 |

COMPARATIVE EXAMPLE 1

A reaction was conducted in the same manner as in Example 1 except that a spherical silica gel (obtained by calcination at 500° C. for 2 hours) was used as the catalyst and p-cresol was used in place of phenol. After 1 hour from the start of raw materials feeding, the reaction product was analyzed by gas chromatography. As a result, the conversion of p-cresol was as low as 2 mole % and no intended product was detected.

As is clear from the above Examples and Comparative Example, in the present process, an alkyl ether of a phenol can be obtained from a phenol and an alcohol at a selectivity and a yield both far higher than in conventional processes, and there occurs substantially no formation of dialkyl ether (by-product) from the raw material alcohol. Consequently, the present process has merits of high recovery ratio of unreacted alcohol and stable catalyst activity over a long period of time. Therefore, the process of the present invention is very useful for industrial production of an alkyl ether of a phenol.

What is claimed is:

1. A process for producing an alkyl ether of a phenol by reacting a phenol with an alcohol in the presence of a catalyst, wherein the catalyst is an oxide represented by the following general formula (1):

$$MaXbZcOd$$

wherein M is an alkali metal; X is silicon and/or zirconium; Z is at least one element selected from Y, La, Ce, Ti, V, Nb, Ta, Cr, Mo, W, B, Al, Ga, In, Tl, Ge, Sn, Pb, P, Sb and Bi; O is oxygen; and a, b, c and d are atom numbers of individual elements with a proviso that when a is 1, b is 1–500, c is 0–1 and d is a number determined by the values of a, b and c and the bonding states of the individual elements.

2. A process according to claim 4, wherein the phenol is a phenol represented by the following general formula (2):

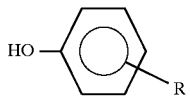

(2)

wherein R is a hydrogen atom, an alkyl group having 1–4 carbon atoms, an alkoxyl group having 1–4 carbon atoms, a hydroxyl group, a phenyl group, a nitro group, a benzyl group or a halogen atom, or a xylenol.

3. A process according to claim 1, wherein the alcohol is a monovalent aliphatic alcohol.

4. A process according to claim 1, wherein in the catalyst of the formula (1) X is silicon.

5. A process according to claim 1, wherein in the catalyst of the formula (1) X is zirconium.

6. A process according to claim 4 or 5 wherein in the formula (1) in Zc, c is 0.

7. A process for producing an alkyl ether or a phenol by reacting a phenol with an alcohol in the presence of a catalyst, wherein the catalyst is an oxide represented by the following general formula (1):

$$MaXbZcOd$$

(1)

wherein M is an alkali metal selected from the group consisting of Cs, Li, Na, K and Rb; X is silicon and/or zirconium; Z is at least one element selected from Y, La, Ce, Nb, W, B, Al and P; O is oxygen; and a, b, c and d are atom numbers of individual elements with a proviso that when a is 1, b is 1–200, c is 0–1 and d is a number determined by the values of a, b and c and the bonding states of the individual elements.

8. A process according to claim 7, wherein the phenol is a phenol represented by the following general formula (2):

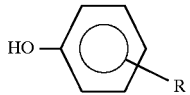

(2)

wherein R is a hydrogen atom, an alkyl group having 1–4 carbon atoms, an alkoxyl group having 1–4 carbon atoms, a hydroxyl group, a phenyl group, a benzyl group or a halogen atom.

9. A process according to claim 7, wherein the alcohol is an alkyl alcohol having 1–4 carbon atoms.

10. A process according to claim 7, wherein in the catalyst of the formula (1) X is silicon.

11. A process according to claim 7, wherein in the catalyst of the formula (1) X is zirconium.

12. A process according to claim 7, wherein in the catalyst of the formula (1) M is Cesium.

13. A process according to claim 7, wherein the a phenol is a member selected from the group consisting of phenol, cresol, methoxy phenol, benzyl phenol, xylenol, catechol, resorcinol and hydroquinone.

14. A process according to claim 7, wherein in the formula (1) M is cesium and X is silicon, wherein the a phenol is selected from the group consisting of phenol, cresol, xylenol and catechol, and the alcohol is an alkyl alcohol having 1–4 carbon atoms.

15. A process according to claim 14, wherein in the formula (1) in Zc, c is 0.

* * * * *